(12) United States Patent
Kaizik et al.

(10) Patent No.: US 8,143,468 B2
(45) Date of Patent: Mar. 27, 2012

(54) PROCESS FOR PREPARING 3-METHYLBUT-1-ENE

(75) Inventors: Alfred Kaizik, Marl (DE); Klaus-Diether Wiese, Haltern am See (DE); Dietrich Maschmeyer, Recklinghausen (DE); Dieter Hess, Marl (DE); Wilfried Bueschken, Haltern am See (DE); Franz Nierlich, Marl (DE)

(73) Assignee: Evonik Oxeno GmbH, Marl (DE)

( * ) Notice: Subject to any disclaimer, the term of this patent is extended or adjusted under 35 U.S.C. 154(b) by 445 days.

(21) Appl. No.: 12/300,224

(22) PCT Filed: May 11, 2007

(86) PCT No.: PCT/EP2007/054576
§ 371 (c)(1),
(2), (4) Date: Nov. 10, 2008

(87) PCT Pub. No.: WO2008/006633
PCT Pub. Date: Jan. 17, 2008

(65) Prior Publication Data
US 2009/0163687 A1 Jun. 25, 2009

(30) Foreign Application Priority Data
Jul. 11, 2006 (DE) .......... 10 2006 031 964

(51) Int. Cl.
*C08F 110/08* (2006.01)
*C07C 5/27* (2006.01)

(52) U.S. Cl. .......... 585/665; 585/670; 585/667; 585/17; 585/882; 585/327; 526/348.6; 526/336

(58) Field of Classification Search .......... 585/665, 585/670, 667, 17, 885, 327; 526/348.6, 336
See application file for complete search history.

(56) References Cited

U.S. PATENT DOCUMENTS

| 5,061,755 A | 10/1991 | Suga et al. |
| 5,344,805 A | 9/1994 | Khare et al. |
| 5,430,220 A | 7/1995 | Khare et al. |
| 6,960,699 B2 | 11/2005 | Totsch et al. |
| 2004/0122278 A1 | 6/2004 | Powers |
| 2007/0106102 A1 | 5/2007 | Caers et al. |
| 2007/0135665 A1 | 6/2007 | Wiese et al. |

FOREIGN PATENT DOCUMENTS

| EP | 0 623 383 | 11/1994 |
| EP | 0 369 213 | 7/1996 |
| JP | 3 28213 | 2/1991 |
| JP | 3 68613 | 3/1991 |
| RU | 2 032 649 | 4/1995 |
| WO | 2005 028404 | 3/2005 |
| WO | 2005 080302 | 9/2005 |
| WO | WO/2005/080302 | * 9/2005 |

OTHER PUBLICATIONS

Marchetti, M. et al., "A protein-rhodium complex as an efficient catalyst for two-phase olefin hydroformylation", Tetrahedron Letters, Pergamon, vol. 41, pp. 3717-3720, XP-002449558, (2000).

Leconte, M. et al., "Stoichiometric and Catalytic Homologation of Olefins on the Fischer-Tropsch Catalysts $Fe/SiO_2$, $Ru/SiO_2$, $Os/SiO_2$, and $Rh/SiO2$. Mechanistic Implication in the Mode of C—C Bond Formation", J. Am. Chem. Soc., vol. 106, No. 4, pp. 1141-1142, (1984).

U.S. Appl. No. 12/307,600, filed Jan. 6, 2009, Grass, et al.

* cited by examiner

*Primary Examiner* — Robert D. Harlan
(74) *Attorney, Agent, or Firm* — Oblon, Spivak, McClelland, Maier & Neustadt, L.L.P.

(57) ABSTRACT

The present invention relates to the preparation of 3-methylbut-1-ene from a hydrocarbon stream I comprising isobutene by feeding a hydrocarbon stream II which comprises at least 70% by mass of isobutene in relation to the olefins present in the hydrocarbon stream and which has been obtained from hydrocarbon stream I or is identical to it to a process step for hydroformylation in which isobutene is hydroformylated in the presence of a rhodium catalyst, hydrogenating the aldehyde obtained from the hydroformylation of isobutene to the corresponding alcohol and preparing 3-methylbut-1-ene by water elimination from the alcohol.

20 Claims, No Drawings

PROCESS FOR PREPARING 3-METHYLBUT-1-ENE

The present invention relates to the preparation of 3-methylbut-1-ene by an at least three-stage synthesis from a hydrocarbon stream comprising isobutene, and to the use of 3-methylbut-1-ene.

$C_5$ olefins, especially methylbutenes, are valued feedstocks in industry. Particularly 2-methylbut-1-ene is a frequently used feedstock in the perfume industry and for preparing isoprene. 3-Methylbut-1-ene can be utilized theoretically as a monomer or comonomer for preparing polymers or copolymers. Industrially prepared polymers of 3-methylbut-1-ene are virtually unknown, since 3-methylbut-1-ene is not available in large amounts. In principle, 3-methylbut-1-ene is present in $C_5$ fractions, for example light gasoline. However, the content of 3-methylbut-1-ene in such fractions is only approx. 1 to 5% by mass. In addition, the isolation of 3-methylbut-1-ene from such fractions is relatively complicated.

The prior art describes some processes for preparing 3-methylbut-1-ene. Methylbutenes can be prepared industrially, for example, by metathesis reactions. For instance, DE 199 32 060 describes the preparation of pentenes and methylbutenes starting from a hydrocarbon stream comprising $C_4$-olefins.

Numerous Japanese applications to Mitsubishi Chemical Industry, for example JP 62-108827, describe the preparation of 3-methylbut-1-ene by partial hydrogenation of isoprene.

U.S. Pat. No. 6,570,033 describes bisphosphite-metal complexes which can be used for the hydroformylation of a large number of olefins. It is stated, inter alia, that isobutene can be hydroformylated. The preparation of 3-methylbut-1-ene is not mentioned.

WO 2005/080302 describes the preparation of olefins having 8 to 12 carbon atoms from olefins having 4 to 6 carbon atoms by metathesis. In this process, a $C_4$ hydrocarbon stream is first hydroformylated, the hydroformylation products are hydrogenated, and water is eliminated from the resulting alcohols. In the hydroformylation, described in the example, of raffinate I which comprises 28.10% by mass of 1-butene and 45.54% by mass of isobutene, a product mixture which comprises only 3% by mass of 3-methylbutanal is obtained. The hydrogenation to 3-methylbutan-1-ol was dispensed with and, instead of this, commercially purchasable 3-methylbutan-1-ol was used to prepare 3-methylbut-1-ene.

It is not possible with any of the processes described in the prior art to prepare 3-methylbut-1-ene from customary technical $C_4$ hydrocarbon streams in a simple manner and with satisfactory conversions.

It was therefore an object of the present invention to provide a simple and economically viable process for preparing 3-methylbut-1-ene from $C_4$ hydrocarbon streams available industrially in large amounts, which avoids one or more of the disadvantages of the processes described in the prior art.

It has now been found that, surprisingly, 3-methylbut-1-ene can be prepared in a particularly simple manner from technical hydrocarbon streams by feeding a hydrocarbon stream which comprises at least 70% by mass of isobutene in relation to the olefins present in the hydrocarbon stream to a hydroformylation in which isobutene is hydroformylated in the presence of a rhodium catalyst, the resulting 3-methylbutanal is hydrogenated to 3-methylbutan-1-ol, and water is eliminated from the 3-methylbutan-1-ol.

The present invention accordingly provides a process for preparing 3-methylbut-1-ene from a hydrocarbon stream I comprising isobutene, which is characterized in that a) a hydrocarbon stream II which comprises at least 70% by mass of isobutene in relation to the olefins present in the hydrocarbon stream and which has been obtained from hydrocarbon stream I or is identical to it is fed to a process step for hydroformylation in which isobutene is hydroformylated in the presence of a rhodium catalyst, b) the aldehyde obtained in step a) from the hydroformylation of isobutene is hydrogenated to the corresponding alcohol, and c) 3-methylbut-1-ene is prepared by water elimination from the at least one alcohol obtained in process step b).

The present invention likewise provides a mixture comprising 3-methylbut-1-ene and 2-methylbut-1-ene, 2,2-dimethylprop-1-ene and/or 3-methylbut-2-ene, the proportion by mass of 3-methylbut-1-ene being at least 90% by mass and the proportion by mass of 2-methylbut-1-ene, 2,2-dimethylprop-1-ene and/or 3-methylbut-2-ene being less than 10% by mass.

The present invention also provides for the use of the inventive mixture as a monomer or comonomer in polymerization, and of polymers prepared using inventive 3-methylbut-1-ene.

The advantage of the process according to the invention is that 3-methylbut-1-ene can be prepared in a simple manner from $C_4$ hydrocarbon streams obtainable in large amounts in industry. When the hydrocarbon streams used contain a suitably high concentration of isobutene, these hydrocarbon streams can be sent directly to the hydroformylation. When hydrocarbon streams which have a concentration of less than 70% by mass of isobutene in relation to the olefins present in the stream are used, it is possible to obtain hydrocarbon streams with suitable concentration therefrom in a simple manner by processes tested on the industrial scale.

When hydrocarbon streams which have a high concentration of isobutene are used in the process according to the invention, it is possible to dispense with a complicated aftertreatment of the 3-methylbut-1-ene obtained in process step c). This is the case especially when pure isobutene or a hydrocarbon stream which comprises more than 99% by mass of isobutene based on the $C_4$-olefins present is used.

The 3-methylbut-1-ene prepared in accordance with the invention or the mixture which comprises 3-methylbut-1-ene and has been prepared in accordance with the invention also has the advantage that it can be used directly, in particular without complicated purification processes, in a metallocene-catalysed copolymerization process in which 3-methylbut-1-ene is copolymerized with ethene or propene, especially with ethene. This is surprising, since a high activity decrease of the catalyst is frequently observed in the case of direct use of commercially available 3-methylbut-1-ene.

The invention makes use of the processes of hydroformylation, hydrogenation and water elimination of olefins, which are known per se. The inventive connection of the individual reaction steps to give a process for preparing 3-methylbut-1-ene achieves the advantages mentioned.

The process according to the invention and the products prepared with it will be described by way of example hereinafter without any intention that the invention be restricted to these exemplary embodiments. When ranges, general formulae or compound classes are specified below, these are not only intended to encompass the particular ranges or groups of compounds which are mentioned explicitly but also all sub-ranges and sub-groups of compounds which can be obtained by removing individual values (ranges) or compounds. When documents are cited hereinafter, their contents shall be included in their entirety in the disclosure content of the present document.

In the process according to the invention for preparing 3-methylbut-1-ene from a hydrocarbon stream I comprising isobutene, a) a hydrocarbon stream II which comprises at least 70% by mass of isobutene in relation to the olefins present in the hydrocarbon stream and which has been obtained from hydrocarbon stream I or is identical to it is fed to a process step for hydroformylation in which isobutene is hydroformylated in the presence of a rhodium catalyst,
b) the aldehyde obtained in step a) from the hydroformylation of isobutene is hydrogenated to the corresponding alcohol, and
c) 3-methylbut-1-ene is prepared by water elimination from the at least one alcohol obtained in process step b).

In process step a), preference is given to using a hydrocarbon stream II which comprises at least 85% by mass, preferably 95% by mass and more preferably 98% by mass of isobutene based on the olefins present. It may be particularly advantageous when a hydrocarbon stream II is used which comprises at least 85% by mass, preferably 95% by mass, more preferably 98% by mass and most preferably 99% by mass of isobutene based on the total mass of the hydrocarbon stream. It may be very particularly advantageous to use pure isobutene as the hydrocarbon stream. The use of a hydrocarbon stream II which has a maximum content of isobutene allows a stream which comprises 3-methylbut-1-ene, contains only a low level of by-products/impurities and can be fed directly as a reactant to a polymerization/copolymerization to be obtained in process step c).

The hydrocarbon streams I or II which comprise isobutene and can be used in the process according to the invention may stem from a wide variety of different sources. The most significant source for $C_4$ olefins is the $C_4$ cut of crack petroleum from steamcrackers. After extraction of the butadiene (for example by extractive distillation) or its selective hydrogenation to an n-butene mixture, a hydrocarbon mixture (raffinate I or hydrogenated crack-$C_4$) is prepared therefrom, which typically contains isobutene, 1-butene and the two 2-butenes. Another raw material for $C_4$-olefins is the $C_4$ cut from FCC plants. $C_4$-olefins prepared by Fischer-Tropsch synthesis are likewise a suitable feedstock after selective hydrogenation of the butadiene present therein to n-butenes. In addition, olefin mixtures which are obtained by dehydrogenating $C_4$ hydrocarbons or by metathesis reaction, or other technical olefin streams, may be suitable feedstocks.

The hydrocarbon stream I or II used may in particular be a mixture which comprises olefins having 3 to 5 carbon atoms. The hydrocarbon stream I or II used, especially hydrocarbon stream II, are preferably mixtures which comprise exclusively $C_4$ hydrocarbons. The hydrocarbon stream I or II used may in particular be a mixture which comprises isobutene and linear butenes or consists thereof. The hydrocarbon stream I or II used, especially hydrocarbon stream I, may preferably be a $C_4$ cut selected from raffinate I, selectively hydrogenated crack-$C_4$, $C_4$ cuts from FCC plants or $C_4$ olefins prepared by Fischer-Tropsch synthesis. The hydrocarbon stream I used is preferably those technical $C_4$ cuts which have an isobutene content of greater than 3% by mass, preferably greater than 10% by mass and more preferably greater than 20% by mass.

Frequently, the hydrocarbon stream I which is to be used in the process according to the invention has an isobutene content which does not correspond to the specification for the hydrocarbon stream II. In this case, preference is given to performing, before process step a), a process stage 1) in which a hydrocarbon stream II which has a higher concentration of isobutene and is fed to process step a) is obtained from the hydrocarbon stream I comprising isobutene.

When the hydrocarbon stream I also comprises dienes, especially 1,3-butadiene, in addition to olefins, the majority of the butadiene can be removed in a preliminary step before the actual process stage 1). The dienes can be removed, for example, by extraction or extractive distillation from hydrocarbon stream I, or the dienes present in hydrocarbon stream I can be hydrogenated selectively to linear butenes, for example down to a residue concentration of approx. 2000 ppm by mass. What remains in both cases is a hydrocarbon stream I which has a maximum of 2000 ppm by mass, if any, of dienes.

Suitable process stages 1) are all processes which enable the concentration of isobutene in hydrocarbon streams. For example, process stage 1) may have one or more thermal separating stages in which compounds other than isobutene are removed. Such thermal separating stages may, for example, be distillations. For instance, all other accompanying substances apart from 1-butene can be removed from the isobutene by distillation from a hydrocarbon stream I which also comprises 1-butene, 2-butene, butane and isobutane as well as isobutene. When the mass ratio of 1-butene to isobutene in such a hydrocarbon stream I is, for example, 1:3, the removal of all further constituents from the hydrocarbon stream I alone is sufficient to obtain a hydrocarbon stream II which has a content of isobutene of at least 75% by mass in relation to the olefins present.

In a preferred embodiment of the process according to the invention, the isobutene present in the hydrocarbon stream I is enriched in process stage 1) by converting the 1-butene present in the hydrocarbon stream I to cis- or trans-2-butene by isomerization, especially by hydroisomerization. Such a hydroisomerization can be performed, for example, in a reactive distillation column. The reaction mixture obtained in the isomerization can then be separated in a simple manner thermally, preferably by distillation, into a fraction which comprises isobutene and is obtained as the top product in the distillation, and a fraction which comprises 2-butenes and is obtained as the bottom fraction in the distillation. A process for hydro-isomerization suitable as process stage 1) is described, for example, by OXENO Olefinchemie GmbH in WO 03/035587.

The isobutene-comprising fraction thus obtained can be fed as hydrocarbon stream II to process step a) of the process according to the invention. The hydrocarbon stream II obtained in this embodiment of the process according to the invention preferably has a content of isobutene, based on the mass of the hydrocarbon stream II, of at least 75% by mass, preferably of 75 to 98% by mass and more preferably of 80 to 95% by mass.

A further possibility of performing process stage 1) may consist in converting isobutene or one or more of the compounds present in hydrocarbon stream I chemically to compounds which can be removed easily from other constituents in the hydrocarbon stream I. The removal can in turn be effected thermally or, for example, mechanically, for example by filtration, if a solid is obtained in the reaction. When the isobutene is converted to a compound in the reaction, preference is give to preparing such a compound which can be obtained again in a simple manner from the isobutene.

In the process according to the invention, preference is given to performing a process stage 1) which comprises the process steps of 1a) reacting isobutene present in the hydrocarbon stream I comprising isobutene with a compound V to obtain a product P,
1b) removing product P from the hydrocarbon stream I,
1c) cleaving product P into isobutene and compound V and
1d) removing the isobutene from compound V to obtain a hydrocarbon stream II.

In the performance of process steps 1a) and/or 1c), it may be advantageous where at least one reactive distillation column is used. The use of a reactive distillation column allows the conversion to be increased by virtue of product being removed from the reaction mixture continually during the reaction and the equilibrium thus being shifted.

In process step 1a), preference is given to using a compound V which is selected from water and alcohol, especially methanol or ethanol. Preference is given to preparing tert-butanol (TBA) by the reaction of the isobutene present in hydrocarbon stream I with water, said tert-butanol being removable in a simple manner, for example thermally, preferably by distillation, from hydrocarbon stream I. Isobutene and water can be obtained again therefrom by a cleavage of TBA. Thermal removal, for example, of the water from the isobutene affords hydrocarbon stream II which contains almost exclusively isobutene. The preparation of TBA from hydrocarbon streams comprising isobutene has long been known. The cleavage of TBA to isobutene and water has also long been known.

The reaction of the hydrocarbon stream I comprising isobutene with water can be effected, for example, as in WO 99/33775, DE 30 25 262, DE 103 30 710 or EP 1 616 848 and the documents cited there. Reference is made explicitly to the aforementioned patents, and their disclosure content shall be encompassed by the disclosure content of the present invention.

The reaction of isobutene with water is effected preferably at a temperature of 30 to 120° C., preferably at a temperature of 35 to 70° C. When the reaction is effected in a plurality of reactors connected in series, it may be advantageous when they are operated at different temperatures. For example, in the case of four reactors connected in series, the first can be operated at a mean temperature of 67 to 70° C., the second at a mean temperature of 53 to 56° C., the third at a mean temperature of 42 to 46° C. and the fourth reactor at 42 to 38° C.

The inventive reaction of isobutene with water can be performed at a pressure equal to or above the vapour pressure of the starting hydrocarbon mixture at the particular reaction temperature, preferably a pressure below 4 MPa. In order to avoid evaporation problems in the reactors, the pressure should be 0.2 to 0.4 MPa higher than the vapour pressure of the reaction mixture.

The catalysts used in the TBA synthesis are preferably acidic ion exchange resins, more preferably solid ion exchange resins with sulphonic acid groups. Suitable ion exchange resins are, for example, those which are prepared by sulphonating phenol/aldehyde condensates or cooligomers of aromatic vinyl compounds. Examples of aromatic vinyl compounds for preparing the cooligomers are: styrene, vinyltoluene, vinylnaphthalene, vinyl-ethylbenzene, methylstyrene, vinylchlorobenzene, vinyl-xylene and divinylbenzene. In particular, the cooligomers which are formed by reacting styrene with divinylbenzene are used as a precursor for the preparation of ion exchange resins with sulphonic acid groups. The resins may be prepared in gel, macroporous or sponge form. Strongly acidic resins of the styrene-divinylbenzene type are sold, inter alia, under the following trade names: Duolite C20, Duolite C26, Amberlyst 15, Amberlyst 35, Amberlite IR-120, Amberlite 200, Dowex 50, Lewatit SPC 118, Lewatit SPC 108, Lewatit K2611, Lewatit K2631, OC 1501, Lewatit K2671, Lewatit K2629 or Lewatit K2431. The trade names or parts thereof may be registered trade marks of the manufacturers.

In the process according to the invention, the ion exchange resins are preferably used in their H form in the TBA synthesis. The ion exchange capacity is preferably 2 to 7 eq/kg, in particular 3 to 6 eq/kg (based on moist commercially available resin).

Very particular preference is given to using macroporous resins, for example Lewatit SCP 118, Lewatit SCP 108, Lewatit K2631, Amberlyst 15 or Amberlyst 35. Optionally, the ion exchange resins may be used as shaped bodies, for example cylinders, rings or spheres. The particle size of the industrial resins is generally between 0.5 and 2 mm. The particle size distribution may also be selected to be wider or narrower. For example, it is also possible to use ion exchange resins with very uniform particle size (monodisperse resins).

The removal of the TBA in step b), which was obtained as the product P in process step 1a), can be effected, for example, thermally. Preference is given to feeding the reaction mixture obtained from process step 1a) to a distillation column which preferably works at or below the pressure of the TBA synthesis, but at least at a pressure of above 0.1 MPa. In the distillation, the top product obtained is a hydrocarbon mixture which consists of unconverted isobutene and of the "inert" hydrocarbons introduced with the reactants. The bottom product obtained is an aqueous tert-butanol solution. The configuration and the operation of such distillations is within the ability of the average person skilled in the art and will not be explained in detail here.

When process step 1a) is performed using a reactive distillation column, process step 1b) may be integrated in process step 1a), or be performed simultaneously with process step 1a) in the reactive distillation column.

The hydrocarbon mixture removed may be worked up to further products of value. When, for example, raffinate I or selectively hydrogenated $C_4$ cut has been used as the reactant, the top product contains linear butenes and also isobutane and n-butane as well as unconverted isobutene. The remaining isobutene can be removed from this mixture, for example, by reaction with alcohol to give alkyl tert-butyl ether. In the remaining raffinate, the linear butenes—optionally after removal of 1-butene—can be converted to di-n-butene and their higher oligomers. Another use of the isobutene-free mixture is the workup to pure 1-butene.

A portion of the aqueous tert-butanol solution obtained can be recycled into the process. The other portion can be used as such in process step 1c) or can be worked up, for example thermally, to pure tert-butanol and an azeotrope of water and tert-butanol.

The cleavage of the TBA in process step 1c) can be effected in a manner known per se. The cleavage can be performed in liquid phase over acidic catalysts, especially over acidic ion exchange resins. Such a process is described by U.S. Pat. No. 4,423,271. The cleavage can, though, also be performed in the gas phase. Such a process, in which the cleavage is effected over acidic aluminas, is described, for example, in U.S. Pat. No. 3,665,048. Preference is given to effecting the TBA cleavage in at least one reactive distillation column. Such a process is described in EP 0 726 241. Particular preference is given to effecting the TBA cleavage in at least one fixed bed reactor which is operated quasi-isothermally. Such a process is described in EP 1 489 062. Reference is made explicitly to the aforementioned patents whose disclosure shall be included in the disclosure content of the present invention.

Process step 1c) of the process according to the invention is performed, in the case of cleavage of TBA, preferably at a temperature of from 80 to 150° C., preferably from 100 to 120° C. The pressure in the TBA cleavage is preferably 0.5 to 2.5 MPa, the pressure preferably being selected to be sufficiently high that isobutene formed in the reactors or in the reaction zones of the reactors remains dissolved virtually completely and essentially homogeneously in the reaction mixture without formation of a gas phase.

The catalysts used in the TBA cleavage are preferably acidic ion exchange resins, as have been described above for the TBA preparation.

The removal of the isobutene in process step 1d) can be effected as described in U.S. Pat. No. 4,423,271, U.S. Pat. No. 3,665,048, EP 0 726 241 or EP 1 489 062. Preference is given to effecting the water removal as described in EP 1 489 062 in at least two columns. The reaction mixture obtained from the TBA cleavage is worked up preferably by removing the predominant portion of the isobutene as an isobutene/water azeotrope from the reactor effluent in a first column via the top. After removal of some of the water, for example by phase separation, virtually water-free isobutene can be obtained by azeotropic distillation in a second column from the top product of the first column. The configuration and the operation of such distillations is within the ability of the average person skilled in the art and will not explained in detail here.

The isobutene thus obtained can be fed as the hydrocarbon stream II to process step a) of the process according to the invention. The hydrocarbon stream II obtained in this embodiment of the process according to the invention preferably has a content of isobutene, based on the mass of the hydrocarbon stream II, of at least 85% by mass, preferably 90 to 99.99% by mass and more preferably of 95 to 99.8% by mass.

In a particularly preferred embodiment of the process according to the invention, the isobutene present in hydrocarbon stream I can be removed in process stage 1) by the reaction of the isobutene present in hydrocarbon stream I with alcohol to give alkyl tert-butyl ether (ATBE) which can be removed in a simple manner, for example thermally, preferably by distillation, from the hydrocarbon stream I. Cleavage of the ATBE allows isobutene and alcohol to be obtained again therefrom. Removal, for example by thermal means, of the alcohol from the isobutene then affords a hydrocarbon stream II which contains almost exclusively isobutene. The preparation of ATBE, especially of methyl tert-butyl ether (MTBE) and ethyl tert-butyl ether (ETBE) from hydrocarbon streams comprising isobutene by reacting them with methanol or ethanol has long been known. The cleavage of ATBE, especially of MTBE or ETBE, to isobutene and the corresponding alcohols has also long been known.

For the reaction of isobutene with alcohols, especially with methanol to give methyl tert-butyl ether, various process variants have been developed (cf.: Ullmann's Encyclopedia of Industrial Chemistry, Online Version, 2004, Wiley & Sons, under Methyl tert-butyl ether, and literature cited there; Obenaus, Fritz; Droste, Wilhelm, Erdoel & Kohle, Erdgas, Petrochemie (1980), 33 (6), 271-275: DE 26 29 769; DE 28 53 769). The documents EP 0 048 893 and DE 25 21 964 describe processes for preparing ATBE. The documents U.S. Pat. No. 3,726,942, U.S. Pat. No. 3,846,088, U.S. Pat. No. 4,334,964, U.S. Pat. No. 4,544,776, DE 30 15 882 and WO 2004/007412 describe processes for preparing MTBE, and the documents EP 0 071 032, DE 10 2005 062699 and DE 10 2005 062722 describe processes for preparing ETBE. All of the processes mentioned can be used as process step 1a) in the process according to the invention. Reference is made explicitly to the aforementioned patents and their disclosure shall be included in the disclosure content of the present invention.

The conversion of isobutene in hydrocarbon stream I in process step 1a) can be performed in one or more reactor(s). Preference is given to using at least two fixed bed reactors. The reactors used may be conventional fixed bed reactors, for example tube bundle reactors, adiabatic fixed bed reactors or circulation reactors. They may be operated with or without partial recycling, in which case the recycle stream can optionally be cooled.

The reactors are operated preferably at temperatures of 10 to 160° C., preferably of 30 to 110° C. and more preferably of 60 to 80° C. The pressure in the reactors, especially in the fixed bed reactors, is preferably 0.5 to 5 MPa, preferably 1 to 2 MPa.

The molar ratio of alcohol to isobutene is preferably 10:1 to 0.9:1, preferably 5:1 to 1:1 and more preferably 2:1 to 1:1.

The catalyst used in the preparation of ATBE in process step 1a) is preferably a firm solid which is soluble neither in the feedstock mixture nor in the product mixture and has acidic sites on its surface. The catalyst should not release any acidic substances to the product mixture under reaction conditions because this can lead to yield losses. The activity of the catalysts is preferably selected such that they catalyse the addition of alcohol to isobutene under reaction conditions but barely catalyse the addition to linear butenes. Moreover, the catalysts should catalyse the oligomerization of linear butenes and dialkyl ether formation from two molecules of alcohol used to a minimum extent, if at all.

The solid catalysts used may, for example, be zeolites, acid-activated bentonites or aluminas, sulphonated zirconium oxides, montmorillonites or acidic ion exchange resins. A group of acidic catalysts preferred in the process according to the invention is that of solid ion exchange resins, especially those having sulphonic acid groups. Suitable ion exchange resins are, for example, those which are prepared by sulphonating phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers which are formed by reacting styrene with divinylbenzene can be used as the precursor for the preparation of ion exchange resins with sulphonic acid groups. The resins may be prepared in gel, macroporous or sponge form. The properties of these resins, especially specific surface area, porosity, stability, swelling or shrinkage, and exchange capacity can be varied by the preparation process.

In the process according to the invention, the ion exchange resins can be used in their H form in process step 1a) in the preparation of ATBE. Strongly acidic resins of the styrene-divinylbenzene type are sold, inter alia, under the following trade names: Duolite C20, Duolite C26, Amberlyst 15, Amberlyst 35, Amberlite IR-120, Amberlite 200, Dowex 50, Lewatit SPC 118, Lewatit SPC 108, K2611, K2621, OC 1501.

The pore volume is preferably 0.3 to 0.9 ml/g, in particular 0.5 to 0.9 ml/g. The particle size of the resin is preferably 0.3 mm to 1.5 mm, in particular 0.5 mm to 1.0 mm. The particle size distribution can be selected to be narrower or wider. For example, it is possible to use ion exchange resins with very uniform particle size (monodisperse resins). The capacity of the ion exchanger is, based on the supply form, preferably 0.7 to 2.0 eq/l, in particular 1.1 to 2.0 eq/l, or preferably 0.5 to 5.5 mol/kg, in particular 0.8 to 5.5 mol/kg (the capacity data in mol/kg are based in each case on the ion exchange resin dried to constant weight in a hot nitrogen stream at, for example, 105° C.).

In a preferred embodiment of process step 1a), the addition of the alcohol to the isobutene is performed in the presence of an acidic catalyst in such a way that at least one reactive stage is performed as a reactive distillation. Particular preference is given to performing the acid-catalysed etherification in process step 1a) in at least two reaction stages, preference being given to performing at least one reaction stage, more preferably the last reaction stage, as a reactive distillation. In the fixed bed reactor(s), a reaction mixture which, with regard to its isobutene, alcohol and tert-butyl ether concentration, is close to the thermodynamic equilibrium, is first prepared over an acidic catalyst from the hydrocarbon stream I and the alcohol. The conversion of the isobutene is preferably greater than 90%. This mixture is fed into the reactive distillation column in the next/last reaction stage, where a further portion of the isobutene is converted to the ether.

The reactive distillation column can be operated preferably at pressures, measured at the top of the column, of 0.3 to 2.5 MPa, preferably 0.5 to 1.5 MPa and more preferably of 0.7 to 1.0 MPa. The reaction of the isobutene with alcohol to give the corresponding tertiary butyl ether is effected in the reactive distillation preferably at a temperature of 10 to 140° C., preferably of 40 to 90° C. and more preferably of 60 to 80° C. (temperature in the region of the column in which the catalyst is disposed. The bottom temperature of the column may be significantly higher).

The reaction mixture obtained from process step 1a) is fed to process step 1b) to remove the ATBE as the product P from the residual hydrocarbon stream I. It may be advantageous to free the ATBE of impurities, especially of olefins or hydrocarbons, substantially completely in process step 1b).

Process step 1b) may be performed as an independent process step. Preference is given to performing process step 1a) thermally, especially as a single-stage or multistage distillation. The configuration and the operation of such distillations is within the ability of the average person skilled in the art and will not be explained in detail here.

Process step 1b) can, though, also be present within process step 1a) when a reactive distillation is used as the last reaction stage in process step 1a). In that case, the bottom product obtained from the distillation column is ATBE which may optionally be purified by means of one or more further distillations. In this case, process step 1b) is performed simultaneously with process step 1a) in the reactive distillation column. The ATBE is obtained as the bottom product of the reactive distillation column and can be worked up further by further distillation steps. The remaining hydrocarbon stream I is present essentially in the top product in the reactive distillation.

Complete removal of the ATBE from the alcohol used is not absolutely necessary in process step 1b). Instead, it is possible to use the ATBE obtained after the removal of the residual hydrocarbon stream I, i.e. in particular ETBE or MTBE, which still contains alcohol directly in step 1c). In this way, a complicated purification stage can be dispensed with.

The cleavage of ATBE, for example MTBE or ETBE, in process step 1c) to obtain isobutene can be effected generally in two different variants. Firstly, the cleavage can be performed in the liquid phase over acidic ion exchange resins, as described, for example, in DE 35 09 292 A1 or DE 36 10 704 A1, or over acidic aluminas, as disclosed, for example, in DD 240 739 A1. Secondly, the cleavage reaction can be performed over acidic catalysts in the gas/liquid phase in a type of combined reactive distillation column, as disclosed in EP 0 302 336 A1 or DE 4 322 712. EP 0 302 336 A1 describes the elimination of methanol from MTBE over an acidic ion exchange resin which is positioned in the column bottom. In DE 4 322 712, the tertiary ether is fed to a reactive distillation column above the reaction zone, the rectifying section of the column serving for isobutene purification, while methanol is removed from the MTBE/methanol azeotrope in the stripping section of the column. Preference is given to cleaving ATBE as described in EP 1 149 814 and to cleaving MTBE as described in WO 04/018393 and the documents cited there. A further although less preferred possibility is the performance of the ATBE cleavage in the gas phase. All of the known processes can be used as process step 1c) in the process according to the invention. Reference is made explicitly to the aforementioned patents, and their disclosure shall be included in the disclosure content of the present invention.

The ATBE cleavage can be performed in one or more reactors. When a plurality of reactors are used, they can be connected to one another in series or parallel or both in series and in parallel. It is possible to use different reactor types, for example fixed bed reactors or tube bundle reactors or kettle reactors. The reactor(s) may be operated isothermally, polytropically or adiabatically, in straight pass or with external recycle.

Process step 1c) in the cleavage of ATBE, especially of MTBE or ETBE, is performed preferably at a temperature of 60 to 200° C., preferably 80 to 125° C. and more preferably at a temperature of 105 to 115° C. When a plurality of reactors are used, the temperatures may independently be the same or different. The pressure at which process step 1c) is performed is preferably 0.1 to 1.0 MPa, preferentially 0.3 to 0.7 MPa. The catalyst used is preferably a cation exchange resin, especially a cation exchange resin having sulphonic acid groups.

In a preferred embodiment of process step 1c), the cleavage of the ATBE is performed in the presence of an acidic catalyst in such a way that at least one reaction stage is performed as a reactive distillation. Particular preference is given to performing the cleavage in process step 1c) in at least two reaction stages, preference being given to performing at least one, more preferably the last, reaction stage as a reactive distillation.

The preferred working range of the reactive distillation is at a pressure between 0.1 and not more than 1 MPa, preferably at a pressure of 0.3 to 0.7 MPa. When the catalyst used is, for example, a cation exchange resin, considerable elimination of sulphonic acid groups from the resin surface is to be expected at over 125° C., so that deactivation of the catalyst occurs gradually. It is recommended here not to exceed a reaction temperature of 105 to 115° C.

The catalyst used in the ATBE cleavage in inventive process step 1c) may in particular be those ion exchange resins which are prepared by sulphonating phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers which are formed by reacting styrene with divinylbenzene are used as a precursor for the preparation of ion exchange resins with sulphonic acid groups. The resins may be prepared in gel, macroporous or sponge form. Strongly acidic resins of the styrene-divinylbenzene type are sold, inter alia, under the following trade names: Duolite C20, Duolite C26, Amberlyst A15, Amberlyst A35, Amberlyst 36, Amberlite IR-120, Amberlite 200, Dowex 50, Lewatit K2431, Lewatit K2441, Lewatit K2621, Lewatit K2629, Lewatit K2641.

The properties of these resins, especially specific surface area, porosity, stability, swelling and shrinkage, and exchange capacity, can be varied by the preparation process. Optionally, it is also possible to use commercial macroporous cation exchange resins which have been modified by partial ion exchange or by thermal desulphonation.

When a reactive distillation is performed in inventive process step 1c), preference is given to using structured catalytic multipurpose packings, as described, for example, in U.S. Pat. No. 5,348,710, EP 0 950 433, EP 0 428 265, EP 433 222. Such structured packings in the context of the present invention are, for example, commercially available as Katapak® from Sulzer AG, Katamax® from Koch-Glitsch or Multipak® from Montz GmbH. These are produced, for example, from sheets, preferably from black steel, stainless steel, Hastelloy, copper or aluminium, or structured fabric webs.

The reaction mixture obtained from process step 1c) is fed to process step 1d) for the removal of the isobutene from the compound V.

Process step 1d) can be performed as an independent process step. In that case, it is preferably performed thermally, in particular as a single-stage or multistage distillation. The configuration and the operation of such distillations are within the ability of the average person skilled in the art and are not explained here in detail.

Process step 1d) may, though, also already be present in process step 1c) when the last reaction stage used in process step 1c) is a reactive distillation. In that case, the top product obtained from the distillation column is isobutene which, if appropriate, can be purified by means of one or more further distillations.

The hydrocarbon stream II obtained from the process step 1d) can be used as the starting material in process step a) of the process according to the invention. The hydrocarbon stream II obtained in this embodiment of the process according to the invention preferably has a proportion of isobutene, based on the mass of the hydrocarbon stream II, of at least 85% by mass, preferably from 90 to 99.99% by mass and more preferably 95 to 99.8% by mass.

Process Stage a) (Hydroformylation)

In process step a), a hydrocarbon stream II which comprises at least 70% by mass of isobutene in relation to the olefins present in the hydrocarbon stream and which has been obtained from the hydrocarbon stream I or is identical to it is fed to a hydroformylation in which isobutene is hydroformylated in the presence of a rhodium catalyst.

The hydroformylation of the isobutene in the hydrocarbon stream II can be effected in one stage or a plurality of stages. When further olefins in addition to isobutene are present in the hydrocarbon stream, a catalyst is required for the hydroformylation which is suitable for hydroformylating the double bond of isobutene.

The olefins which are possibly present in the hydrocarbon stream II differ considerably in their reactivity in the hydroformylation. In general, olefins with terminal double bonds are more reactive than olefins with internal double bonds, and linear olefins more reactive than branched olefins. 1-Butene is thus more reactive than isobutene, and isobutene is more reactive than the two 2-butenes. This different reactivity can be utilized in order to obtain a high proportion of products which have formed by terminal hydroformylation, i.e. essentially 3-methylbutanal and not 2,2-dimethylpropanal is obtained from isobutene. This connection can be utilized in the present process to the effect that, in the hydroformylation, only the α-olefins (1-butene, isobutene), especially the isobutene, but not the 2-butenes, are converted to the corresponding aldehydes. Any unconverted 2-butenes can be removed from the reaction mixture obtained from process step a) and sent to a further use.

The hydroformylation in process step a) is preferably performed under such conditions that the isobutene is converted highly selectively to 3-methylbutanal. The catalyst used in process step a) is therefore preferably a rhodium complex catalyst which has organophosphorus ligands.

The catalysts used may, for example, be compounds which comprise rhodium and trivalent organic phosphorous compounds, especially phosphines or phosphites, as ligands. When phosphines are used as a catalyst component, the reaction can be performed in homogeneous phase (analogously to the UCC process EP 0 562 451) or in heterogeneous phase (analogously to the Rhone-Poulenc-Ruhrchemie process DE 026 27 354, EP 0 562 451). Owing to the simpler implementation, process step a) is performed preferably by the first process.

The reaction temperatures in the hydroformylation are preferably 70 to 150° C., preferably 100 to 130° C. The process pressures are preferably 2 to 20 MPa, preferably 3 to 6 MPa. The hydroformylating agent used is preferably a mixture of carbon monoxide and hydrogen in a molar ratio of carbon monoxide to hydrogen of 1:10 to 10:1, preferably in a molar ratio of 1.1:1 to 1:1.1 and more preferably of 1:1. The rhodium concentration in the hydroformylation mixture is preferably 5 to 500 ppm by mass, preferably 10 to 200 ppm by mass. Per mole of rhodium, preference is given to using 1 to 50 mol, preferably 5 to 30 mol, of organophosphorous ligand. The reaction can be performed continuously or batchwise. However, preference is given to a continuous procedure.

Suitable catalysts are, for example, also rhodium complex catalysts which contain mono- or multidentate phosphite ligands. The ligands and complex catalysts which may be used are in particular those as have been described in EP 0 155 508 (UCC), EP 0 213 639 (UCC), EP 0 214 622 (UCC), EP 0 471 071 (BASF), EP 1 099 677 (OXENO), EP 1 099 678 (OXENO) or EP 1 201 675 (OXENO). Particularly suitable rhodium complex catalysts with monodentate phosphite ligands are, for example, triaryl phosphites whose aryl groups both have a bulky group in the ortho-position to the phosphite oxygen and are substituted in the m- or p-position, for example tris(2,4-di-tert-butylphenyl) phosphite. Such a tris-(2,4-di-tert-butylphenyl) phosphite can be purchased, for example, under the name ALKANOX 240 from the Great Lakes Chemical Corporation. The hydroformylation of isobutene using a catalyst system which consists of rhodium and a bisphosphite is described, for example, in the patents U.S. Pat. No. 4,668,651, U.S. Pat. No. 4,769,498 and WO 85/03702. Reference is made explicitly to all documents mentioned, and their disclosure content shall form part of the subject matter of the present description. Particular preference is given to performing the hydroformylation in the presence of a monodentate phosphite ligand, in particular in the presence of tris(2,4-di-tert-butylphenyl) phosphite, as a ligand.

Optionally, the hydroformylation of the 1-olefins in the multiphase system, in which reactant, product and synthesis gas are dispersed in a continuous catalyst phase, can be performed with high superficial velocities. Such processes are described, for example, in DE 199 25 384 A1 and DE 199 57528 A1, to which reference is made here explicitly.

The hydroformylation of the α-olefins can be performed in one stage or two stages. The two-stage performance of the hydroformylation is advantageous especially when the hydrocarbon stream II comprises more than 5% by mass, preferably more than 10% by mass and in particular between 10 and 25% by mass of 1-butene based on the olefins present in the hydrocarbon stream II. In the two-stage hydroformylation, predominantly 1-butene is converted in the first reactor and essentially isobutene in the second reactor. The same catalyst or different catalysts may be used in the two reactors. When the same catalyst is used, combined catalyst workup is possible.

In the hydroformylation of isobutene and if appropriate of 1-butene just described in process step a), any 2-butenes or saturated hydrocarbons present and any unconverted isobutene and/or 1-butene remain in the hydrocarbon stream II. This mixture can be removed from the aldehydes present and sent to a further use, for example likewise to a hydroformylation.

Optionally, this mixture, which contains mainly 2-butenes as olefins, can be oligomerized to predominantly $C_8$-olefins, for example using nickel-containing fixed bed catalysts.

The catalyst can be removed from the hydroformylation mixtures obtained in process step a) by known processes. For example, in processes in which the rhodium catalyst is present in homogeneous form in the reaction mixture, the catalyst can be removed thermally, for example by distillation. In the case of reaction in heterogeneous phase (two liquid phases), the catalyst can be removed, for example, by phase separation (Ed. B. Cornils, W. A. Herrmann, Applied Homogeneous Catalysis with Organic Compounds, Vol. 1, p. 80, VCH-Verlag, 1996).

After a decatalyization, the hydroformylation mixtures may preferably either be used directly in process step b) or else be separated into two or more fractions by distillation or by other separating methods. In particular, it may be advantageous to work up the hydroformylation mixture so as to obtain one or more fractions comprising essentially aldehydes.

Process Step b) (Hydrogenation)

The hydroformylation mixtures which have preferably been decatalysed, or the aldehydes or aldehyde-comprising fractions removed therefrom by a separation process, for example distillation, are hydrogenated in process step b) of the process according to the invention. The hydrogenation forms the corresponding saturated alcohols from the aldehydes; in particular, the alcohol 3-methylbutanal is formed from the 3-methylbutanal obtained from isobutene in process step a).

For the hydrogenation, the catalyst used in process step b) may, for example, be nickel, copper, copper/nickel, copper/chromium, copper/chromium/nickel, zinc/chromium, nickel/molybdenum catalysts. The catalysts may be unsupported, or the hydrogenation-active substances or their precursors may be applied to supports, for example silicon dioxide or aluminium oxide. Preferred catalysts over which the hydroformylation mixtures are hydrogenated each comprise 0.3 to 15% by mass of copper and nickel, and also, as activators, 0.05 to 3.5% by mass of chromium and advantageously 0.01 to 1.6% by mass, preferably 0.02 to 1.2% by mass, of an alkali component on a support material, preferably aluminium oxide and silicon dioxide. Suitable hydrogenation catalysts are described, for example, in EP 0 326 674. The quantitative data are based on the catalyst which is yet to be reduced. The alkali component is optional. The catalysts are advantageously used in a form in which they offer a low flow resistance, for example in the form of granules, pellets or shaped bodies, such as tablets, cylinders, strand extrudates or rings. They are appropriately activated before use, for example by heating in a hydrogen stream.

The hydrogenation, preferably a liquid phase hydrogenation, is preferably performed at a total pressure of 0.5 to 50 MPa, preferably of 1.5 to 10 MPa. A hydrogenation in the gas phase can also be performed at relatively low pressures, in which case correspondingly large gas volumes are present. Where a plurality of hydrogenation reactors are used, the total pressures in the individual reactors may be the same or different within the pressure limits mentioned. The reaction temperatures in the hydrogenation in process step b) in liquid or gaseous phase may generally be 120 to 220° C., in particular 140 to 180° C. Such hydrogenations are described, for example, in the patent applications DE 198 42 369 and DE 198 42 370, to which reference is made here explicitly.

In the process according to the invention, the hydrogenation is performed preferably in the presence of water. The water required may be present in the reactor feed. However, it is also possible to feed water into the hydrogenation apparatus at a suitable point. In gas phase hydrogenation, water is appropriately supplied in the form of steam. A preferred hydrogenation process is liquid phase hydrogenation with addition of water, as described, for example, in DE 100 62 448. Particular preference is given to performing hydrogenation at a water content of 0.05 to 10% by mass, in particular 0.5 to 5% by mass, very particularly 1 to 2.5% by mass. The water content is determined in the hydrogenation effluent.

The mixtures obtained from the hydrogenation may either be used directly in process step c), or else be separated into two or more fractions by distillation or by other separating methods. In particular, it may be advantageous to work up the hydrogenation mixture in such a way that one or more fractions comprising essentially alcohols having the same number of carbon atoms are obtained.

When, proceeding from a $C_4$ hydrocarbon cut, some of the linear olefins present therein are internally hydroformylated, it may be appropriate to remove some or all of the 2-methylbutanol formed therefrom by hydrogenation.

Process Step c) (Water Elimination)

The corresponding 1-olefins are prepared by water elimination in process step c) from the alcohol mixture or the resulting alcohols or alcohol-comprising fractions obtained after the hydrogenation in process step b).

In the process according to the invention, the dehydration can be performed in the gas phase or liquid/gas mixed phase. Process step c) can be performed continuously or batchwise. Process step c) can be performed over suspended catalysts or catalysts arranged in piece form in the fixed bed. Owing to the simple removal of the reaction products, the water elimination from the reaction mixture is performed preferably over solid catalysts in the temperature range of 200 to 500° C. in the gas phase or gas/liquid mixed phase. Particular preference is given to performing a continuous dehydration over a catalyst arranged in a fixed bed. The catalysts used may be oxides of the alkaline earth metals, of aluminium, of indium, of gallium, of silicon, of scandium, of yttrium, of lanthanum, of titanium, of zirconium, of thorium and of the rare earths. It is also possible to use mixed oxides and combinations of the above oxides. In some catalysts, a certain acidity can be established by adding alkali metal oxides.

The scientific technical literature discloses, for example, the following suitable catalysts:

$NiO/Al_2O_3$; $CuO/Al_2O_3$; $Al_2O_3$ (J. Mol. Catal. A. Chem. (1997), 121 (2-3), p. 157-159);

$ZrO_2$; sulphated $ZrO_2$ (J. Mol. Cat. A. Chem (1997), 118 (1), p. 88-89);

$Al_2O_3$; $CO_2O_3$; $ThO_2$; $In_2O_3$ (J. Catal. (1988), 110 (2), p. 416-418);

$HfO_2/ZrO_2$ (J. Phys. Chem. (1980), 84 (1), 55-56);

$Al_2O_3/Na_2O$; ThO2 (J. Catal. (1981), 68 (2), p. 383-387);

$ThO_2$ (J. Org. Chem. (1967), 32 (11), 3386-3389);

$La_2O_3$ (Z. Phys. Chem. (1985), 144, p. 157-163);

$Ga_2O_3$ (J. Org. Chem. (1977), 44 (13), p. 2142-2145);

$ThO_2$; $Al_2O_3$ (J. Org. Chem. (1972), 37 (8), p. 1240-1244).

Preference is given to selecting the catalysts and the reaction conditions in such a way that the formation of by-products, for example of ethers, and the isomerization of the 1-olefins formed to olefins with internal double bonds is largely prevented. For the preparation of the 1-olefins from the primary alcohols by water elimination in process step c), in the process according to the invention, preference is therefore given to using basic or strongly basic catalysts. The catalysts used may comprise, as main components, aluminium oxide ($Al_2O_3$) and/or zirconium oxide ($ZrO_2$), and also alkali metal and/or alkaline earth metal oxides. As further components, titanium dioxide, silicon dioxide and/or thorium oxide may be present in the catalyst at 0.01 to 3% by mass, preferably 0.5 to 5% by mass.

The proportion of basic metal oxides (hydroxides are converted to oxides) in the catalyst is preferably 0.01 to 10% by mass, more preferably 0.1 to 5% by mass, especially preferably 0.1 to 3% by mass. Preferred alkali metal oxides are sodium oxide and/or potassium oxide. The alkaline earth metal oxides used are preferably magnesium oxide, strontium oxide and/or barium oxide. Particular preference is given to eliminating the water in process step c) over a solid catalyst which consists in a formal sense of aluminium oxide and barium oxide. The catalyst used in process step c) is most preferably a γ-aluminium oxide which has been modified with barium oxide (BaO), and consists in a formal sense of barium oxide and aluminium oxide.

Preference is given to using γ-aluminium oxides having a BET surface area of 80 to 350 $m^2/g$, preferably 120 to 250 $m^2/g$ (determined by $N_2$ absorption to DIN 66131). The catalysts are prepared by known methods. Common methods are, for example, precipitation, impregnation or spraying of a $Al_2O_3$ body with an appropriate salt solution and subsequent calcination.

It may likewise be advantageous when catalysts as described in DE 103 59 628 are used, and which have a content of zirconium dioxide of 80 to 99 parts by mass, of yttrium oxide of 0.5 to 10 parts by mass, and of alkali metal or alkaline earth metal oxides of 0.1 to 3 parts by mass.

The catalysts are preferably used in the form of spheres, tablets, cylinders, strand extrudates or rings.

In the continuous water elimination, different process variants can be used. Process step c) can be performed, for example, adiabatically, polytropically or virtually isothermally, i.e. with a temperature difference of typically less than 10° C. The process step can be performed in one or more stages. In the latter case, all reactors, appropriately tubular reactors, can be operated adiabatically or virtually isothermally. It is likewise possible to operate one or more reactors adiabatically and the others virtually isothermally. Preference is given to operating the water elimination in straight pass. However, it can also be operated with product recycling. In the case of operation in straight pass, the specific catalyst hourly space velocity is 0.01 to 30 kg, preferably 0.1 to 10 kg, of alcohol per kg of catalyst and per hour. In the water elimination in process step c), the temperature in the catalyst layer is preferably 200 to 450° C., in particular 250 to 350° C. The water elimination (dehydration) can be performed under reduced pressure, elevated pressure or at standard pressure.

The reactant of process step c), i.e. the alcohol obtained in process step b), especially 3-methylbutanol, can be conducted into the dehydration reactor in pure form or in dilution. The diluents used may be inert gases or gas mixtures, for example nitrogen, hydrogen, carbon monoxide, carbon dioxide, synthesis gas, methane or steam, or organic solvents which are inert under reaction conditions and can be removed easily from the reaction effluent.

In order to achieve a maximum selectivity for 1-olefin formation, it has been found to be advantageous when the aim is only partial conversion of the alcohol used. Preference is given to performing process step c) in such a way that the conversion in straight pass is 30 to 90%.

The product obtained from process stage c) is a mixture comprising at least one 1-olefin, especially 3-methylbut-1-ene. In process step c), preference is given to obtaining a fraction comprising 1-olefins, from which 3-methylbut-1-ene is removed. The reaction mixture may, if appropriate after water removal, be separated by distillation into starting alcohol, olefins and by-products.

The reaction mixture is preferably separated into fractions comprising the 1-olefin(s) formed, the primary alcohol(s) and if appropriate by-products, for example ethers or carbonyl compounds, for example aldehydes. The separation can be effected, for example, by distillation. The olefin fraction obtained after the separation can be worked up optionally to pure 3-methylbut-1-ene (less than 0.1% by mass of extraneous substances). The alcohol-comprising fraction which comprises the unconverted alcohol is preferably recycled into the dehydration. Any aldehyde formed as a by-product in the dehydration can be reused to give the corresponding alcohol after hydrogenation and thus does not cause any loss. The hydrogenation can be performed in a separate hydrogenation apparatus. However, it may be advantageous to feed the aldehydes obtained as by-products into the hydrogenation preceding the dehydration (process step b). This removal of the aldehydes from the mixture obtained in the dehydration, subsequent hydrogenation and recycling of the alcohols obtained into the dehydration allow olefins to be obtained in a particularly high selectivity in the inventive dehydration.

When the starting material of the process according to the invention which is used in process step a) is, for example, a $C_4$ hydrocarbon mixture which comprises isobutene and linear butenes or consists thereof, hydroformylation, hydrogenation and water elimination (process steps a) to c)) afford a $C_5$ olefin mixture which may comprise the olefins 3-methylbut-1-ene, 1-pentene and if appropriate 2-methylbut-1-ene and 2-methylbut-2-ene. 1-Pentene has a boiling point of 30° C. at standard pressure, 2-methylbut-1-ene a boiling point of 31.2° C., 2-methylbut-2-ene a boiling point of 38° C. and 3-methylbut-1-ene a boiling point of 20.1° C. Owing to the significantly different boiling points, 3-methylbut-1-ene can, after process step c), be removed by distillation easily from the other isomers which are present in the resulting 1-olefin fraction.

The 3-methylbut-1-ene obtained by the process according to the invention can be used as a monomer or comonomer to prepare oligomers or polymers. It can also be used as a starting compound for the preparation of epoxides, ketones, aldehydes, alcohols and carboxylic acids. It can also be used as an alkylating agent or as a component in ene reactions.

The inventive 3-methylbut-1-ene which can be obtained in particular by the process according to the invention contains preferably less than or equal to 10% by mass, preferably less than or equal to 1% by mass and more preferably 0.001 to 1% by mass of 2-methylbut-1-ene, 2,2-dimethylprop-1-ene and/or 3-methylbut-2-ene. A preferred mixture contains 3-methylbut-1-ene and 2-methylbut-1-ene, 2,2-dimethylprop-1-ene and/or 3-dimethylbut-2-ene, the proportion by mass of 3-methylbut-1-ene being at least 90% by mass and the proportion by mass of 2-methylbut-1-ene, 2,2-dimethyl-prop-1-ene and/or 3-methylbut-2-ene being less than 10% by mass. The mixture preferably comprises at least 99% by mass and more preferably 99.000 to 99.999% by mass of 3-methylbut-1-ene and preferably less than or equal to 1% by mass and more preferably 0.001 to 1% by mass of 2-methylbut-1-ene, 2,2-dimethylprop-1-ene and/or 3-methylbut-2-ene, the proportions adding up to 100%. The inventive 3-methylbut-1-ene or the mixture may be used as a monomer or comonomer in the polymerization. In particular, the inventive 3-methylbut-1-ene or the inventive mixture may be used as a comonomer or block comonomer in the polymerization/copolymerization of ethylene or propylene. This use of the inventive 3-methylbut-1-ene or of the mixture allows the corresponding polymers, i.e. homopolymers, copolymers and block copolymers, to be obtained.

The examples which follow are intended to illustrate the process according to the invention without restricting the scope of application which is evident from the description and the claims.

EXAMPLE 1

Hydroformylation

The experiment was performed in an experimental plant consisting of a bubble column reactor, a thin-film evaporator and a distillation apparatus. The isobutene was introduced into the bubble column at the bottom, together with an excess of synthesis gas, and a high-boiling solvent comprising the catalyst. At the top of the reactor, unconverted synthesis gas was removed. The liquid fractions (residual olefin, aldehydes, by-products, high-boiling solvent, catalyst) were passed to the thin-film evaporator which was operated under reduced pressure, such that the aldehyde formed together with the unconverted olefins was separated here from the higher-boiling components in which the catalyst was dissolved. The high-boiling solvent used was dioctyl phthalate which was present in a 20% weight fraction in the reactor, because no high boiler from the process was present on startup of the experiment and would also only be formed to a small degree during the experimental period. The rhodium concentration in the reactor was 30 ppm by mass of rhodium; the ligand added was tris(2,4-di-tert-butylphenyl) phosphite; the molar P/Rh ratio was 20/1. The bubble column was heated externally to a constant 115° C. by means of a jacket; the operating pressure was 5.0 MPa of synthesis gas.

Under the above-specified reaction conditions, an olefin feed of 2 kg/h of isobutene was established. The bubble column reactor had a volume of 2.1 liters.

The assessment of the streams for isobutene and conversion products gave rise to the following product distribution in % by mass.

| | |
|---|---|
| Isobutene | 8.2 |
| Pivalaldehyde | 0.1 |
| 3-Methylbutanal | 90.8 |
| 3-Methylbutanol | 0.3 |
| High boilers | 0.6 |

The conversion of isobutene was 92% at a selectivity for 3-methylbutanal based on isobutene of 99%.

EXAMPLE 2

Hydrogenation of 3-methylbutanal

The unconverted isobutene was distilled off from the product from Example 1. The remaining residue was fractionated into reaction products and dioctyl phthalate with small amounts of high boilers. The distillate had the following composition:

| | |
|---|---|
| Pivalaldehyde | 0.1 |
| 3-Methylbutanal | 99.1 |
| 3-Methylbutanol | 0.3 |
| High boilers | 0.5 |

1 kg of the distillate was admixed with 12 g of water and hydrogenated in a 2 l stirred autoclave at 180° C. over 100 g of a Cu/Cr/Ni catalyst on $Al_2O_3$ support. Based on the catalyst, the catalyst contained 0.3% by mass of Cu, 4.5% by mass of Ni and 0.07% by mass of Cr, and was prepared analogously to Example 1 in EP 0 326 674, except that an $Al_2O_3$ support was used instead of an $SiO_2$ support. After 3 hours, the hydrogenation had ended. After cooling, decompression and removal of the catalyst by filtration, a hydrogenation product with the following composition (calculated without water) was obtained:

| | |
|---|---|
| 2,2-Dimethylpropanol | 0.1 |
| 3-Methylbutanal | 0.1 |
| 3-Methylbutanol | 99.3 |
| High boilers | 0.5 |

EXAMPLE 3

Preparation of a Dehydration Catalyst

The support material used for the preparation of a dehydration catalyst was an acidic γ-aluminium oxide having a $Na_2O$ content of less than 300 ppm by mass from Axens. This aluminium oxide having a BET surface area of 225 m$^2$/g and a pore volume of 0.68 ml/g was present in the form of an extrudate (cylinder with a length of 4-6 mm and a diameter of 1.25 mm). The barium precursor used for the basic modification of the aluminium oxide with barium oxide (BaO) was barium nitrate $Ba(NO_3)_2$.

Before the application of the barium salt, the aluminium oxide was first dried at 90° C. for 5 h in a forced-air drying cabinet. 200 g of the dried strand extrudate were then impregnated in a rotary drum (coating drum) at room temperature with a solution consisting of 130 ml of water and 5.19 g of barium nitrate, with the aid of a spray nozzle.

After the impregnation, the extrudate laden with the barium salt was first dried at 110° C. for 5 h in a forced-air drying cabinet. The subsequent calcination, in which the barium salt is converted to barium oxide or to a barium/aluminium/oxygen compound, was effected in a fluidized bed reactor in an airstream at 450° C. for 10 h. The finished catalyst contained 1.5% by mass of barium compounds, calculated as the barium oxide.

EXAMPLE 4

Preparation of 3-methylbut-1-ene from 3-methylbutan-1-ol

The 3-methylbutan-1-ol obtained in Example 2 was converted in an electrically heated fixed bed flow reactor over the catalyst according to Example 3. Before entry into the reactor, the liquid reactant was evaporated at 220° C. in an upstream evaporator. At a reaction temperature of 340° C., 24 g per hour of 3-methylbutan-1-ol were passed through 15.1 g of catalyst in the gas phase, corresponding to a WHSV value of 1.59 h$^{-1}$. The reaction pressure was 0.15 MPa. The gaseous product was cooled in a condenser and collected in a glass receiver. Calculated without water, the product had the following composition:

| Component | Content [% by mass] |
|---|---|
| 3-Methylbutene-1 | 94.4900 |
| 3-Methylbutene-2 | 3.2157 |
| 2-Methylbutene-1 | 0.6985 |
| Di(3-methylbutyl) ether | 0.1995 |
| 3-Methylbutanol-1 | 0.9105 |
| High boilers | 0.4858 |

EXAMPLE 5

Purification of 3-methylbut-1-ene 10.8 kg of the product obtained in Example 4 were separated by distillation in a fractional distillation in a laboratory apparatus as described below. The normal boiling points of the components involved are listed in the table which follows:

| Component | Normal boiling point [° C.] |
|---|---|
| 3-Methylbutene-1 | 20.0 |
| 3-Methylbutene-2 | 38.5 |
| 2-Methylbutene-1 | 31.2 |
| Di(3-methylbutyl) ether | 130.9 |
| 3-Methylbutanol-1 | 173.3 |
| High boilers | >180 |

As can be seen with reference to the normal boiling points reported, the mixture has a relatively wide boiling range. Azeotropes are not formed, so that concentration of 3-methylbutene-1 is possible by simple batch distillation.

To this end, a glass column consisting of a distillation still with internal evaporator, 3 sections and top condenser was constructed. The column sections had a diameter of 80 mm and were each equipped with 1 m of fabric packing, Sulzer DX® type. According to manufacturer data, this packing type has approx. 20 theoretical plates per meter of packing, so that a total of approx. 60 theoretical plates were available for the distillation. For the cooling of the top condenser, cold water (feed approx. 10° C.), for the bottom heating heat carrier oil was used.

The bottom was filled with 10.8 kg of product. Subsequently, the column was evacuated and heated, and was operated with infinite reflux without product withdrawal. During the distillation, the column was operated at a top pressure of 0.0980 MPa (abs) and a reflux ratio of 1.6 to 1.9. This gave rise to bottom temperatures of approx. 39° C. and top temperatures of approx. 19° C.

The operating mode of the column thus described allowed 9.8 kg of product to be generated from the reactor effluent with the following composition:

| Component | Content [% by mass] |
|---|---|
| 3-Methylbutene-1 | 99.8051 |
| 3-Methylbutene-2 | 0.0001 |
| 2-Methylbutene-1 | 0.1948 |
| Di(3-methylbutyl) ether | |
| 3-Methylbutanol-1 | |
| High boilers | |

The invention claimed is:

1. A process for preparing 3-methylbut-1-ene comprising:
   a) hydroformylating isobutene in the presence of a rhodium catalyst to form an aldehyde, wherein said hydroformylating comprises hydroformylating a hydrocarbon stream II which comprises at least 70% by mass of isobutene in relation to olefins present in the hydrocarbon stream II and which has been obtained from a hydrocarbon stream I comprising isobutene or is identical to the hydrocarbon stream I,
   b) hydrogenating the aldehyde obtained in step a) to form at least one alcohol, and
   c) eliminating water from the at least one alcohol obtained in process step b) to form 3-methylbut-1-ene,
   wherein at least 90% of the isobutene is converted to the aldehyde in step a).

2. The process according to claim 1, wherein the hydrocarbon stream I or II is a mixture which comprises olefins having 3 to 5 carbon atoms.

3. The process according to claim 1, wherein the hydrocarbon stream I or II is a mixture which comprises isobutene and linear butenes.

4. The process according to claim 1, wherein the hydrocarbon stream I or II is a $C_4$ containing stream selected from the group consisting of raffinate I, selectively hydrogenated crack-$C_4$, $C_4$ containing streams from fluid catalytic cracking (FCC plants), and $C_4$ olefins prepared by Fischer-Tropsch synthesis.

5. The process according to claim 1, wherein the hydrocarbon stream I is a $C_4$ containing stream that has an isobutene content of greater than 3% by mass.

6. The process according to claim 1, wherein the hydrocarbon stream II comprises at least 85% by mass of isobutene based on the olefins present in said hydrocarbon stream II.

7. The process according to claim 6, wherein the hydrocarbon stream II comprises at least 95% by mass of isobutene based on the olefins present in said hydrocarbon stream II.

8. The process according to claim 1, wherein before process step a), a process stage 1) is performed, by which a hydrocarbon stream II having a higher concentration of isobutene which is fed to process step a) is obtained from the hydrocarbon stream I comprising isobutene.

9. The process according to claim 8, wherein the process stage 1) comprises:
   1a) reacting isobutene present in the hydrocarbon stream I comprising isobutene with a compound V to obtain a product P,
   1b) removing product P from the hydrocarbon stream I,
   1c) cleaving product P into isobutene and compound V, and
   1d) removing the isobutene from compound V to obtain a hydrocarbon stream II.

10. The process according to claim 9, wherein the compound V in process step 1a) is selected from the group consisting of water and alcohol.

11. The process according to claim 9, wherein a reactive distillation column is used in process step 1a) and/or 1c).

12. The process according to claim 1, wherein the rhodium catalyst is a rhodium complex catalyst which has organophosphorus ligands.

13. The process according to claim 1, wherein a catalyst is used in process step b) and is selected from the group consisting of a nickel catalyst, a copper catalyst, a copper/nickel catalyst, a copper/chromium catalyst, a copper/chromium/nickel catalyst, a zinc/chromium catalyst, and a nickel/molybdenum catalyst.

14. The process according to claim 1, wherein process step c) is performed over a solid catalyst which consists of aluminium oxide and barium oxide.

15. The process according to claim 6, wherein a fraction comprising 1-olefins is obtained after process step c), from which 3-methylbut-1-ene is removed.

16. A mixture comprising 3-methylbut-1-ene and 2-methylbut-1-ene, 2,2-dimethylprop-1-ene and/or 3-methylbut-2-ene, the proportion by mass of 3-methylbut-1-ene being at least 90% by mass and the proportion by mass of 2-methylbut-1-ene, 2,2-dimethylprop-1-ene and/or 3-methylbut-2-ene being less than 10% by mass.

17. 3-Methylbut-1-ene prepared by a process according to claim 1.

18. A monomer or comonomer in a polymerization process comprising the mixture comprising 3-methylbut-1-ene according to claim 16.

19. A comonomer or block comonomer in the polymerization of ethylene or propylene comprising 3-methylbut-1-ene according to claim 16.

20. A polymer prepared using the mixture comprising 3-methylbut-1-ene according to claim 16.

* * * * *